United States Patent [19]

Spitznas

[11] 4,452,514
[45] Jun. 5, 1984

[54] OPTICAL DEVICE FOR IMAGING AN INTERIOR OF AN EYE

[75] Inventor: Manfred Spitznas, Bonn, Fed. Rep. of Germany

[73] Assignee: Optische Werke G. Rodenstock, Munich, Fed. Rep. of Germany

[21] Appl. No.: 365,091

[22] Filed: Apr. 2, 1982

[30] Foreign Application Priority Data

Apr. 2, 1981 [DE] Fed. Rep. of Germany ... 8109993[U]

[51] Int. Cl.³ ........................... A61B 3/10; A61B 3/14
[52] U.S. Cl. ...................................... 351/206; 351/205
[58] Field of Search ................. 350/410; 351/206, 205

[56] References Cited

U.S. PATENT DOCUMENTS 4,134,647  1/1979  Ramos-Caldera ............ 351/205 X

Primary Examiner—John K. Corbin
Assistant Examiner—Rodney B. Bovernick
Attorney, Agent, or Firm—Craig & Burns

[57] ABSTRACT

An optical device for imaging an interior of an eye, especially a retina of the human eye, with the optical device including a front element which acts as an objective and which is adapted to be brought in proximity to the eye, and a single- or multi-element field lens disposed in a common mount. The mount and field lens each include a flattened surface portion extending substantially parallel to a common optical axis of the front element and field lens. The flattened surface portions are disposed so as to permit an introduction of a surgical instrument into the eye during eye surgery such as, for example, vitrectomy.

17 Claims, 3 Drawing Figures

OPTICAL DEVICE FOR IMAGING AN INTERIOR OF AN EYE

The present invention relates to an optical device and, more particularly, to an optical device for imaging an interior of an eye, especially a retina of a human eye during eye surgery, with the device including a front lens acting as an objective, with the front lens being adapted to be brought near to the eye, and a field lens, with the front and field lens being held in a common mount.

Various types of loupe-like eyeglasses have been proposed for viewing the anterior ocular media, with such glasses being employed especially to look into the iridocorneal angle. A special glass construction of this type, known as a Barkan goniotomy lens is used for surgery in the vicinity of the iridocorneal angle.

In, for example, German Pat. No. 1,188,326 and French Pat. Nos. 2,136,927 and 2,168,842, multi-lens eyeglasses for viewing and imaging the middle and posterior ocular media, especially the retina, have been proposed, with such eyeglasses including a front lens adapted to be brought into the immediate vicinity of the eye, and a single- or multi-element field lens. Eyeglasses of this type are generally employed with an immersion fluid to image the posterior optical media, with the fluid filling a space between the anterior surface of the eye and the front element of the eyeglass.

A disadvantage of the above-proposed construction resides in the fact that it does not permit the use of the instrument for eye surgery, especially for vitrectomy during viewing or imaging.

The aim underlying the present invention essentially resides in providing an optical device for viewing a posterior optical media, with the optical device being usable simultaneously with instruments for eye surgery so as to enable an observation of the surgical procedures.

In accordance with the present invention, a front element and a single-or multi-element field lens are disposed in a common mount with the mount and field lens including a flattened surface portion which preferably runs parallel to a common optical axis of the lenses so as to permit an introduction into the eye of an instrument which is used for eye surgery, such as, for example, vitrectomy.

Advantageously, in accordance with the present invention, the flattened surface portion may form a plane and also include a boundary area of the front element of the optical device.

In accordance with still further features of the present invention, the optical device or eyeglass may be mounted in an adjustable holder in such a manner that it remains in a position relative to the eye which is comfortable for the user. For this purpose, a stand may be provided which may form a portion of the surgical equipment.

Advantageously, in accordance with the present invention, the stand may be adjustable, and the optical device or eyeglass may be mounted in the stand so as to be rotatable about the optical axes of the lenses in order to enable a swiveling or pivoting of the flattened surface portion without changing the position of the image of the interior of the eye.

Preferably, locking means are provided so as to enable the optical device or eyeglass to be fixed in a rotational position comfortable for the user, thereby enabling the user to have both hands free for other activities.

The mount may, in accordance with the present invention, include a cylindrical area with which an internal cylinder of the stand, serving as a receptacle, is associated.

A preferably spring-loaded pin may, in accordance with the present invention, be provided for holding the mount in its receptacle.

Accordingly, it is an object of the present invention to provide an optical device for imaging an interior of the eye, especially the retina of a human eye, which avoids, by simple means, the shortcomings and disadvantages encountered in the prior art.

Another object of the present invention resides in providing an optical device for imaging an interior of an eye, especially the retina of a human eye, which permits an observation of the eye during surgical procedures while allowing the user's hands to remain free in order to handle the surgical instruments.

Yet another object of the present invention resides in providing an optical device for imaging an interior of an eye, especially the retina of a human eye, which permits an introduction of a surgical instrument into the eye when the optical device is in use.

A still further object of the present invention resides in providing an optical device for imaging an interior of an eye, especially the retina of a human eye, which is adjustable so as to enable the optical device to be positioned relative to the eye in a position which is comforatable for the user.

A still further object of the present invention resides in providing an optical device for imaging an interior of the eye, especially the retina of a human eye, which is simple in construction and therefore relatively inexpensive to manufacture.

These and other objects, features, and advantages of the present invention will become more apparent from the following description when taken in connection with the accompanying drawing which shows, for the purposes of illustration only, one embodiment in accordance with the present invention, and wherein.

Figure 1:
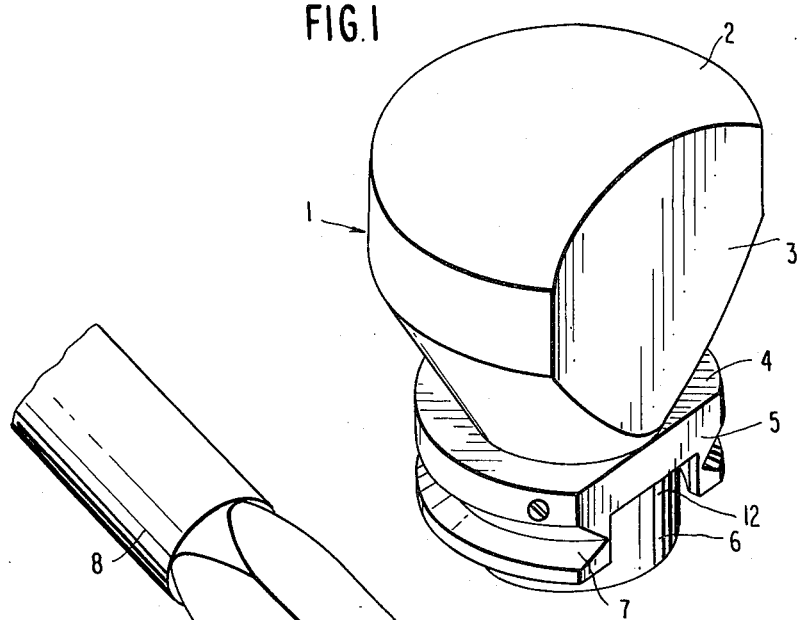
FIG. 1 is a perspective view of an optical device constructed in accordance with the present invention.
Figure 3:
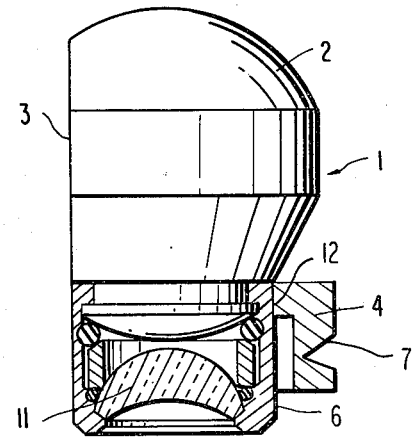
FIG. 3 is a partial cutaway side elevational view of the optical device of the present invention.

Referring now to the drawing wherein like reference numerals are used throughout the several views to designate like parts and, more particularly, to FIGS. 1 and 3, according to these figures, an optical device or eyeglass generally designated by the reference numeral 1 includes a field lens 2 which may, for example, be a single or multi-element lens, with the field lens 2 including a flattened surface portion 3. A mounting means for the optical device includes a mounting ring 4 surrounding a mounting member 12, the mounting member 12 forming a common mounting member for the front element 11 and the field lens 2. The mounting ring 4 is provided with a flattened surface portion 5 disposed in the same plane as the flattened surface portion 3. The flattened surface portion 3 of the field lens 2 and the flattened surface portion 5 of the mounting ring 4 extend in parallel to the optical axis of the field lens 2 and the front element 11.

Figure 2:
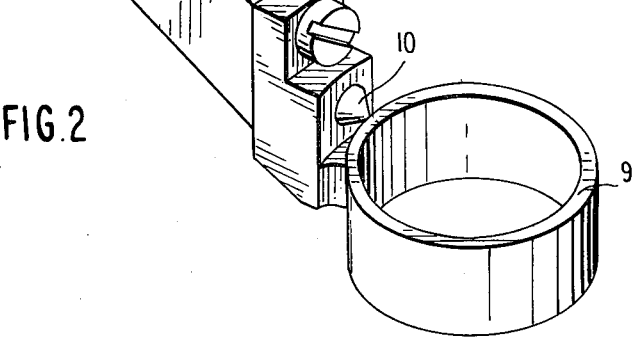
FIG. 2 is a perspective view of a receiving area of a stand for accommodating the optical device of FIG. 1.

As shown most clearly in FIG. 2, a stand forming, for example, a portion of surgical equipment, includes a stand arm 8 having mounted thereon cylindrical guide ring 9 forming a receptacle for accommodating the mounting means of the optical device 1. The mounting member 12 forms a cylindrical extension portion 6 which, in cooperation with the annular groove 7, serves to hold the optical device 1 in the stand arm 8 in such a manner that the optical device 1 may be rotated about the optical axis of the front element 11 and the field lens 2.

To mount the optical device 1, the cylindrical extension portion 6 is inserted into the guide ring 9 and a pin 10 which is preferably spring-loaded engages the annular groove 7 so as to hold and lock the optical device in the stand arm 8.

As shown in the side elevation of FIG. 3, with the flattened surface portion 3 arranged in a viewing direction, a boundary area of the mounting member 12 is also disposed in the same plane as the flattened surface portions 3, 5 of the field lens 2 and the mounting ring 4, respectively.

While I have shown and described only one embodiment in accordance with the present invention, it is understood that the same is not limited thereto but is susceptible of numerous changes and modifications as known to those skilled in the art, and I therefore do not wish to be limited to the details shown and described herein but intend to cover all such changes and modifications as are encompassed by the scope of the appended claims.

I claim:

1. An optical device for imaging an interior of an eye, the device including a front element which acts as an objective and which is adapted to be brought in proximity to the eye, a field lens, and a common mounting means for mounting the front element and field lens, characterized in that the mounting means and the field lens each include a flattened surface portion extending substantially parallel to a common optical axis of the front element and the field lens, the flattened surface portions are disposed so as to permit an introduction of a surgical instrument into the eye during eye surgery.

2. An optical device according to claim 1, characterized in that the device is adapted to image a retina of the human eye, and in that the eye surgery is a vitrectomy.

3. An optical device according to one of claims 1 or 2, characterized in that each of the flattened surface portions is a planar surface portion.

4. An optical device according to claim 3, characterized in that the flattened surface portion includes a boundary area of the front element.

5. An optical device according to claim 4, characterized in that an adjustable stand means is provided for holding the optical device, means are provided on the stand means for accommodating the mounting means so as to enable the optical device to be rotated about the optical axes of the field lens and front element.

6. An optical device according to claim 5, characterized in that the mounting means includes a cylindrical portion, the means for accommodating the mounting means includes an internal cylindrical receptacle for receiving the cylindrical portion of the mounting means.

7. An optical device according to claim 6, characterized in that means are provided for holding the mounting means in the internal cylindrical receptacle.

8. An optical device according to claim 7, characterized in that the means for holding includes at least one spring-loaded pin engageable with the mounting means.

9. An optical device according to claim 6, characterized in that means are provided for locking the mounting means in the internal cylindrical receptacle.

10. An optical device according to claim 1, characterized in that an adjustable stand means is provided for holding the optical device, means are provided on the stand means for accommodating the mounting means so as to enable the optical device to be rotated about the optical axes of the field lens and front element.

11. An optical device according to one of claims 1 or 10, characterized in that the mounting means includes a cylindrical portion, the means for accommodating the mounting means includes an internal cylindrical receptacle for receiving the cylindrical portion of the mounting means.

12. An optical device according to claim 11, characterized in that means are provided for holding the mounting means in the internal cylindrical receptacle.

13. An optical device according to one of claims 1 or 10, characterized in that means are provided for locking the mounting means in the means for accommodating the mounting means.

14. An optical device according to claim 1, characterized in that the mounting means includes a cylindrical extension portion, a mounting ring surrounding the cylindrical extension portion and an annular groove provided in the mounting ring, an adjustable stand means is provided for holding the optical device, a cylindrical receptacle is mounted on the stand means for accommodating the cylindrical extension portion, and in that means cooperable with the annular groove are provided for holding the optical device on the stand means so as to enable the optical device to be rotated about the optical axis of the front element and field lens.

15. An optical device according to claim 14, characterized in that the flattened surface portion of the mounting means is formed by an outer surface portion of the cylindrical extension portion and a flat surface provided on the mounting ring.

16. An optical device according to claim 2, in which the field lens is a single-element field lens.

17. An optical device according to claim 2, in which the field lens is a multiple-element field lens.

* * * * *